United States Patent [19]

Lappas et al.

[11] 4,025,533

[45] May 24, 1977

[54] 5-BROMO-5-NITRO-2-ALKYLSUBSTITUTED-1,3-DIOXANE

[75] Inventors: Lewis C. Lappas; Clarence A. Hirsch, both of Indianapolis, Ind.

[73] Assignee: Eli Lilly and Company, Indianapolis, Ind.

[22] Filed: Apr. 14, 1976

[21] Appl. No.: 676,944

Related U.S. Application Data

[63] Continuation of Ser. No. 514,166, Oct. 11, 1974, abandoned, which is a continuation-in-part of Ser. No. 427,945, Dec. 26, 1973, abandoned, which is a continuation-in-part of Ser. No. 333,418, Feb. 16, 1973, abandoned.

[52] U.S. Cl. .............................. 260/340.7; 424/278

[51] Int. Cl.$^2$ .................. C07D 319/06; A01N 9/28
[58] Field of Search .................................. 260/340.7

[56] References Cited

OTHER PUBLICATIONS

Kedzierski, et al., "Rocz. Chem." 1972, 46(a) pp. 1559–1565.

*Primary Examiner*—Anton H. Sutto
*Attorney, Agent, or Firm*—Ralph W. Ernsberger; Everet F. Smith

[57] ABSTRACT

5-Bromo-5-nitro-2-alkylsubstituted-1,3-dioxanes, such as 5-bromo-2-methyl-5-nitro-1,3-dioxane, novel antimicrobials with activity against both bacteria and fungi.

5 Claims, No Drawings

5-BROMO-5-NITRO-2-ALKYLSUBSTITUTED-1,3-DIOXANE

CROSS-REFERENCE

The application is a continuation of Ser. No. 514,166, filed Oct. 11, 1974, which is a continuation-in-part of Ser. No. 427,945, filed Dec. 26, 1973, which is a continuation-in-part of Ser. No. 382,992, filed July 26, 1973, which is a continuation-in-part of Ser. No. 333,418, filed Feb. 16, 1973, all now abandoned.

BACKGROUND OF THE INVENTION

1. Field of the Invention

This invention relates to organic chemistry. More particularly, the instant invention pertains to the novel compounds, 5-bromo-5-nitro-2-alkylsubstituted-1,3-dioxanes, exceptionally active antimicrobials.

2. Prior Art

A wide variety of antimicrobials are known. A large number of antibiotics and synthetic organic chemicals are useful as bacteriostats, bacteriocides, fungistats, fungicides et seq. Many of these effective antimicrobials have an important role in controlling the microorganisms that infect man. Some have a broad scope of activity while others find a place in a narrow range of applications. A few are even limited to a single utility.

Antimicrobial preservatives are recognized as important ingredients in cosmetic creams used as bases for facial make-up. These creams are generally comprised of an oil in water emulsion. The ingredients furnish a fertile substrate for microorganisms such as bacteria and fungi. Moreover, as both oil and water are present, the choice of an appropriate preservative requires attention to the need for antimicrobial activity in both systems. Inasmuch as it is likely that an effective antimicrobial works best when it is soluble in the substrate to be protected, it is important that a preservative for such a cosmetic cream should have an effective solubility in both oil and water.

A preservative which has been employed in cosmetic creams with some degree of success is 2-bromo-2-nitropropane-1,3-diol. However, this compound has a deficiency in that it is chemically unstable towards alkali.

A more recent introduction to the number of compounds useful for preserving cosmetic creams is the subject of British Pat. No. 1,250,725, and U.S. Pat. No. 3,772,443, 5-bromo-5-nitro-1,3-dioxane. While this compound does possess chemical stability towards alkali and has a relatively wide spectrum of activity, it induces irritation and sensitization in a significant number of human subjects. Therefore, the search for alkali stable compounds having both oil and water solubility and a lower incidence of human irritation and sensitization has continued.

Accordingly, it is an object of this invention to provide alkali stable compounds having suitable oil and water solubility which are effective at relatively low concentrations against a wide range of both bacteria and fungi, and have a low incidence of irritation and sensitization of human subjects.

SUMMARY

New compounds, 5-bromo-5-nitro-2-alkylsubstituted-1,3-dioxanes have now been discovered that are effective at low concentrations against a broad spectrum of bacteria and fungi, and have a low incidence of irritation and sensitization of human subjects. Such compounds have excellent chemical stability from pH 5–9, and are soluble in both water and oil (mineral) to the extent of 1.1 to 1.5 percent. Cosmetic creams can be effectively preserved by the incorporation therein of as little as 0.01 percent of these novel compounds.

DESCRIPTION OF THE PREFERRED EMBODIMENTS

In one embodiment of this invention, the novel compounds are of the formula

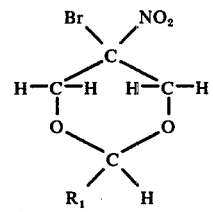

wherein $R_1$ is methyl, ethyl, n-propoyl, or isopropyl.

The useful compounds of the instant invention can be prepared utilizing 2-bromo-2-nitropropane-1,3-diol as the starting material. The compound, 2-bromo-2-nitropropane-1,3-diol is commercially available under the trademark Bronopol, and can be prepared in several different ways. One efficient process involves using nitromethane as a reactant and combining it with formaldehyde to form 2-nitropropane-1,3-diol, converting the latter to the sodium salt and brominating such salt to get 2-bromo-2-nitropane-1,3-diol. Preparation 1 exemplifies the preparation of 2-bromo-2-nitropropane-1,3-diol from nitromethane.

PREPARATION 1

Twenty grams (0.5 mole) of sodium hydroxide were dissolved in 400 ml. of water and the solution was cooled to 10° C. To 74 ml. of 35% formaldehyde (1.0 mole) were added 76 ml. of the previously prepared sodium hydroxide solution. Then to the combined formaldehyde-sodium hydroxide solution were added dropwise 27 ml. (0.5 mole) of nitromethane, all the while holding the reaction temperature between 25°–30° C. by immersing the reaction vessel in an icewater bath. The reaction of the nitromethane and formaldehyde was catalyzed by the sodium hydroxide and 2-nitropropane-1,3-diol was formed, but not isolated. The diol was then converted to the sodium salt by adding the remainder of the previously prepared sodium hydroxide solution to the reaction vessel at 20° C. and the reaction mixture was stirred at room temperature and atmospheric pressure for ½ hour.

Three-hundred milliliters of ethyl acetate were cooled to −5° C. utilizing an ice-acetone bath. To the cooled ethyl acetate were added 25.5 ml. (0.5 mole) of bromine in a slow steady stream holding the temperature at 5° C. or below. Then the previously prepared sodium 2-nitropropane-1,3-diol reaction mixture was slowly added to the ethyl acetatebromine mixture holding the temperature in the 5°–10° C. range. The reaction mixture was stirred for 5 minutes at room temperature and atmospheric pressure, after which the pH was adjusted to 2.0 with 6N HCl. Two-hundred grams of sodium chloride were added to the reaction mixture driving the 2-bromo-2-nitropropane-1,3-diol into the ethyl acetate layer.

The ethyl acetate fraction was separated from the water fraction and dried over magnesium sulfate, and filtered. The ethyl acetate was removed from the filtrate under vacuum and the resulting dry solids were washed with methylcyclohexane and again reduced to dryness. Eighty-three and one-tenth gram (83.1% yield) of 2-bromo-2-nitropropane-1,3-diol were recovered which had a melting point of 108°–114° C.

The novel compounds of this embodiment of the present invention can be prepared by reacting an appropriate aldehyde with the 2-bromo-2-nitropropane-1,3-diol, from Preparation I, in an acidic environment. The preparation of 5-bromo-2-methyl-5-nitro-1,3-dioxane is exemplified in Example 1.

EXAMPLE 1

Forty grams (0.2 mole) of 2-bromo-2-nitropropane-1,3-diol were suspended in 200 ml. of benzene and about 0.3 g. of p-toluene sulfonic acid was added. The mixture was cooled in an ice-water bath and a condenser attached to the reaction vessel. About 13.5 g. (0.3 mole) of acetaldehyde were slowly added through the condenser and the reaction mixture was stirred for 30 minutes. A Dean-Stark trap was connected and the mixture warmed slowly, then heated to reflux until water no longer was evolved. (About 4 ml. of water was evolved in 1.5 hours). The solution was filtered and evaporated on a rotating evaporator at about 45° C. A dark oil residue was obtained, which was vacuum distilled at 0.25 mm. Thirty-six and one-half grams (85% yield) of 5-bromo-2-methyl-5-nitro-1,3-dioxane were obtained having a boiling range at 0.25 mm. of from 72°–74° C. The NMR and IR were consistent with the structure, and an elemental analysis disclosed the following percentage composition:
 C: calc. 26.57, found 26.85;
 H: calc. 3.57, found 3.85;
 N: calc. 6.20, found 6.04;
 Br: calc. 35.35, found 35.21.

The compound, 5-bromo-2-methyl-5-nitro-1,3-dioxane is a water clear, colorless liquid at room temperature, and does not solidify at −10° C. It is chemically stable at pH's from 5.0 to 9.0 and has an acrid pungent odor faintly resembling bromine.

EXAMPLE 2

The compound 5-bromo-2-ethyl-5-nitro-0245 1,3-dioxane was prepared following the procedure outlined in Example 1 by substituting propionaldehyde for the acetaldehyde. The NMR was consistent with the structure, and an elemental analysis disclosed the following percentage composition:
 C: calc. 30.02, found 30.24;
 H: calc. 4.20, found 4.24;
 N: calc. 5.83, found 5.92;
 Br: calc. 33.29, found 32.99.

The white crystalline material had a melting point of 58°–59° C. The compound is chemically stable at pH's from 5–9 and has the same acrid pungent odor faintly resembling bromine that is exhibited by the methyl derivative.

EXAMPLE 3

The compound 5-bromo-5-nitro-2-n-propyl-1,3-dioxane was prepared following the procedure outline in Example 1 by substituting n-butyraldehyde for the acetaldehyde. The NMR and IR were consistent with the structure, and an elemental analysis disclosed the following percentage composition:
 C: calc. 33.09, found 33.32;
 H: calc. 4.76, found 4.63;
 N: calc. 5.51, found 5.66;
 Br: calc. 31.45, found 31.64.

The compound obtained was a colorless oil which, when distilled at 0.005 mm Hg, had a boiling point of 73°–75° C. The oil solidified to a waxy solid on standing at room temperature. The acrid pungent odor of bromine was present.

EXAMPLE 4

The compound 5-bromo-2-isopropyl-5-nitro-1,3-dioxane was prepared following the procedure outline in Example 1 by substituting isobutyraldehyde for the acetaldehyde. The NMR and IR were consistent with the structure, and an elemental analysis disclosed the following percentage composition:
 C: calc. 33.09, found 33.33;
 H: calc. 4.76, found 4.83;
 N: calc. 5.51, found 5.33;
 Br: calc. 31.45, found 31.24.

The compound obtained was a colorless crystalline material which, after recrystallization from a 1:1 isopropanol: water solvent had a melting point of 42°–44° C. The acrid, pungent odor of bromine was present.

The novel compounds of this embodiment of the present invention, exemplified in Examples 1, 2, 3, and 4 can exist as cis- and trans-isomers. The procedure outlined in Example 1 produces a ratio of isomers of about 9:1. It is the intent of this invention to include both geometric isomers as chemical entities as well as the isomeric mixture. Antimicrobial tests on isomeric mixtures of 5-bromo-2-methyl-5-nitro-1,3-dioxane, one high in the cis- form and the other high in the trans-form, showed equal activity, indicating no significant difference in the usefulness of the two geometric isomers. Consequently, the utility tests described hereinafter were conducted employing the isomeric mixture (about 9:1) prepared as detailed in Example 1.

The useful compounds of this invention are highly effective in vitro against a wide spectrum of microbial organisms, both bacteria and fungi. For example, 5-bromo-2-methyl-5-nitro-1,3-dioxane (Compound C) was tested against *Propionibacterium acnes* (formerly called *Corynebacterium acnes*) in a conventional tube dilution test. A simultaneous test was run utilizing 2-bromo-2-nitropropane,1,3-diol (Compound A) and 5-bromo-5-nitro-1,3-dioxane (Compound B) as the antimicrobials. Each compound had a minimum inhibitory concentration of 6.25 mcg/ml against the test organism.

The test against *Propionibacterium acnes* were run anaerobically in the following medium:
 Peptone — 10.0g
 Yeast extract — 10.0g
 Glucose — 10.0g
 Ca $Cl_2$ — 0.2g
 Mg $So_4 \cdot 7H_2O$ — 0.2g
 $K_2HPO_4$ — 1.0g
 $KH_2PO_4$ — 1.0g
 $NaHCO_3$ — 10.0g
 Na Cl — 2.0g
 Distilled water q.s. — 1000 ml
The pH of the medium was 6.9

The in vitro antimicrobial activities of Compounds A, B and C, 5-bromo-2-ethyl-5-nitro-1,3-dioxane (Compound D), 5-bromo-5-nitro-2-n-propyl-1,3-dioxane (Compound E), and 5-bromo-2-isopropyl-5-nitro-1,3-dioxane (Compound F) were determined concurrently against *Pseudomonas aeruginosa, Staphylococcus aureus, Escherichia coli*, and *Steptococcus faecalis* in a conventional tube dilution test. The medium used was antibiotic Number 3 [CFR 436.102(3)] and the concentration of organisms was $10^4$ organisms per ml of medium, with each tube being inoculated with 0.1 ml of inoculum. The figures shown in Table I are the lowest concentrations in the mcg of active compound/ml of medium where no growth occurred in the medium after two days' incubation at 37° C.

TABLE I

In Vitro Antimicrobial Activity
Minimum Inhibitory Concentration, mcg./ml. when tested with —

|  | Pseudomonas aeruginosa | Staphylococcus aureus | Esterichia coli | Streptococcus faecalis |
|---|---|---|---|---|
| Compound A | 12.5 | 25.0 | 12.5 | 25.0 |
| Compound B | 25.0 | 25.0 | 25.0 | 25.0 |
| Compound C | 25.0 | 25.0 | 25.0 | 25.0 |
| Compound D | 50.0 | 25.0 | 25.0 | 25.0 |
| Compound E | 50.0 | 50.0 | 25.0 | 25.0 |
| Compound F | 50.0 | 25.0 | 25.0 | 25.0 |

The antimicrobial activities of Compounds A, B, C, D, E and F were also determined in an agar plate system. The compounds were added to melted and cooled (50° C.) agar in twofold concentration increments from 50 mcg per ml of agar to 1.56 mcg per ml of agar. Antibiotic medium 1 [CFR 436.102(1)] was used for testing of *Pseudomonas aeruginosa, Staphylococcus aureus, Escherichia coli*, and *Streptococcus faecalis*, but antibiotic medium 22 [CFR 436.102(22)] was used for testing of *Candida albicans* and *Aspergillus niger*. Organism suspensions containing $10^6$ organisms per ml were used as stock suspensions. Sterile cotton swabs were dipped in the suspensions and then streaked across the solidified agar. The figures shown in Table II were the lowest concentrations at which no growth occurred after 72 hours at 30° C. These values were interpreted as the minimum inhibitory concentration (MIC).

TABLE II

In Vitro Antimicrobial Activity
Minimum Inhibitory Concentration, mcg./ml. when tested with —

|  | Pseudomonas aeruginosa | Staphylococcus aureus | Escherichia coli | Streptococcus faecalis | Candida albicans | Aspergillus niger |
|---|---|---|---|---|---|---|
| Compound A | 6.25 | 12.5 | 6.25 | 12.5 | >50.0 | >50.0 |
| Compound B | 12.5 | 12.5 | 6.25 | 12.5 | 12.5 | 25.0 |
| Compound C | 25.0 | 12.5 | 12.5 | 12.5 | 6.25 | 12.5 |
| Compound D | 25.0 | 12.5 | 12.5 | 12.5 | 6.25 | 12.5 |
| Compound E | 25.0 | 12.5 | 12.5 | 12.5 | 3.1 | 6.25 |
| Compound F | 25.0 | 12.5 | 12.5 | 25.0 | 6.25 | 12.5 |

Compounds A, B, and C were tested further to determine antifungal activity. Results obtained with 10 fungi are shown in Table III. The compounds were added to melted and cooled (50° C) agar to obtain concentrations of 100, 50, 25, 12.5, 6.25 and 0.0 mcg per ml of agar. After the agar solidified, sterile cotton swabs were dipped in stock suspensions of the organisms ($10^6$ organisms per ml of physiological saline) and then streaked across the agar. After three days' incubation at 25° C, concentrations which prevented growth were recorded as the minimal inhibitory concentration. The composition of the medium used in this study was as follows:

Mannitol — 1.0g
Maltose — 5.0g
Yeast extract — 2.0g
Calcium carbonate — 0.5g
Meer agar — 20.0g
V-8 juice filtrate — 200.0ml
Distilled water q.s. — 1000 ml
The pH was adjusted to 5.7.

TABLE III

In Vitro Antifungal Activity
Minimum Inhibitory Concentration

| ORGANISM | Compound A (mcg./ml.) | Compound B (mcg./ml.) | Compound C (mcg./ml.) |
|---|---|---|---|
| *Aspergillus fumigatus* | <6.25 | <6.25 | <6.25 |
| *Aspergillus terreus* | 25.0 | 25.0 | 12.5 |
| *Penicillium notatum* | 100.0 | 25.0 | 25.0 |
| *Microsporum gypseum* | 50.0 | 50.0 | 100.0 |
| *Saccharomyces pastorianus* | >100.0 | 100.0 | >100.0 |
| *Fusarium oxysporum cubense* | 25.0 | <6.25 | 12.5 |
| *Colletotrichum phomoides* | >100.0 | 100.0 | 100.0 |
| *Botrytis cinerea* | 25.0 | 50.0 | 12.5 |
| *Chaetomium globosum* | <6.25 | <6.25 | <6.25 |
| *Rhodotorula glutinis* | 100.0 | 50.0 | 100.0 |

From the data shown in Tables I, II and III above, it is clear that the novel compounds of the instant invention have antimicrobial and antifungal properties that are consistent with the prior art compounds with which they were compared.

The significant properties which distinguish the useful compounds of this invention from the prior art compounds is the significantly lower irritation and subsequent sensitization of human skin when the compounds are applied to the skin in specially formulated cosmetic creams.

In the instant invention, the 2-methyl derivative of 5-bromo-5-nitro-1,3-dioxane is an especially preferred species because of its superior solubility in water and oil.

An evaluation was made of skin irritating and skin sensitizing properties of the prior art compound 5-bromo-5-nitro-1,3-dioxane and the especially preferred compound of this invention, 5-bromo-2-methyl-5-nitro-1,3-dioxane. The following protocol was followed in testing each compound.

Two-hundred subjects were employed in each investigation. The repeated insult technique was used in the patch test. A different group of subjects were utilized for each evaluation.

The technique used for the patch test called for a series of 9 induction patches of each test material to be placed on each of the subjects. The series was followed 2 weeks later by a single "challenge" patch of each test material to detect skin sensitization.

The series of nine induction patches was applied on Monday, Wednesday and Thursday and allowed to contact the skin for 24 hours, after which time they were removed and the skin sites graded for irritation. Thursday's patches were placed immediately after removal and grading of Wednesday's applications. After the ninth induction patches had been placed, a non-patching period of 2 weeks elapsed before the challenge patches were applied to detect sensitization reactions. For this 24-hour patch, a new skin site was used. This site was invariably chosen adjacent to an induction site; i.e., one where repeated applications had been made during the series of nine induction patches. The challenge applications were graded at 24 and 72 hours after application.

The skin applications for each material were made using oval-shaped adhesive patches (1 × 1¼ inch) with circular gauze centers. The gauze centers were coated with approximately 0.03 ml. of the respective test material just prior to application.

The scoring criteria used for skin irritation reactions and in evaluating the sensitization evidenced on the challenge application follows:

TABLE IV

Human Repeated Insult Patch Test
Scoring Criteria for Skin Reactions

Erythema and Eschar Formation

| | |
|---|---|
| No reaction | 0 |
| Very slight erythema (barely perceptible) | 1 |
| Mild, well-defined erythema | 2 |
| Moderate to severe erythema | 3 |
| Severe erythema (beet redness) to slight eschar formation (injuries in depth) | 4 |
| Total Possible Erythema Score | 4 |

Edema Formation

| | |
|---|---|
| No reaction | 0 |
| Very slight edema (barely perceptible) | 1 |
| Slight edema (edge of area well-defined by definite raising) | 2 |
| Moderate edema (area raised approximately 1 mm) | 3 |
| Severe edema (area raised more than 1 mm and extending beyond area of exposure) | 4 |
| Total Possible Edema Score | 4 |
| Total Possible Primary Irritation Score | 8 |

Four separate formulations of each compound were tested along with two formulations of parabens. These formulations were all cosmetic creams at different concentrations of the active compounds as shown in Table V:

TABLE V

| Test Material | Active Compound | Concentration Percent | Type of Cream |
|---|---|---|---|
| A | 5-bromo-5-nitro- | 0.05 | Nonionic |
| B | 1,3-dioxane | 0.1 | Nonionic |
| C | | 0.05 | Anionic |
| D | | 0.1 | Anionic |
| E | 5-bromo-2-methyl-5- | 0.01 | Nonionic |
| F | nitro-1,3-dioxane | 0.1 | Nonionic |
| G | | 0.01 | Anionic |
| H | | 0.1 | Anionic |
| K | Parabens | 0.6 | Nonionic |
| L | | 0.6 | Anionic |

Table VI below shows a summary of the scores of all the tests:

TABLE VI

Comparison of the Irritation and Sensitization of 5-bromo-5-nitro-1,3-dioxane and 5-bromo-2-methyl-1,3-dioxane in a Human Repeated Insult Patch Test.

5-BROMO-5-NITRO-1,3-DIOXANE

Induction Series of Applications

| | | Total Number of Reactions with Scores of: | | | | | | | | |
|---|---|---|---|---|---|---|---|---|---|---|
| Material | Number of Reactors | 0 | 1 | 2 | 3 | 4 | 5 | 6 | 7 | 8 |
| A | 25 | 1766 | 18 | 3 | 3 | 1 | 1 | 1 | 0 | 0 |
| B | 41 | 1735 | 29 | 12 | 9 | 3 | 3 | 0 | 0 | 2 |
| C | 21 | 1768 | 18 | 6 | 1 | 0 | 1 | 1 | 0 | 0 |
| D | 56 | 1693 | 59 | 23 | 6 | 6 | 2 | 4 | 0 | 0 |
| K | 19 | 1771 | 21 | 5 | 0 | 0 | 0 | 0 | 0 | 0 |
| L | 20 | 1767 | 21 | 5 | 2 | 1 | 1 | 0 | 0 | 0 |

Challenge Application

| | | Total Number of Reactions with Scores of: | | | | | | | | |
|---|---|---|---|---|---|---|---|---|---|---|
| Test Material | Number of Reactors | 0 | 1 | 2 | 3 | 4 | 5 | 6 | 7 | 8 |
| A | 3 | 197 | 0 | 0 | 1 | 1 | 0 | 1* | 0 | 0 |
| B | 11 | 189 | 2 | 2 | 2 | 1 | 1* | 2* | 0 | 1* |
| C | 2 | 198 | 0 | 0 | 1 | 0 | 0 | 1* | 0 | 0 |
| D | 20 | 180 | 1 | 5 | 2 | 5 | 1* | 3* | 1* | 2* |
| K | 2 | 198 | 1 | 0 | 0 | 0 | 0 | 0 | 0 | 0 |
| L | 1 | 199 | 0 | 0 | 0 | 1 | 0 | 0 | 0 | 0 |

*Indicative of skin sensitization

5-BROMO-2-METHYL-5-NITRO-1,3-DIOXANE

Induction Series of Applications

| | | Total Number of Reactions with Scores of: | | | | | | | | |
|---|---|---|---|---|---|---|---|---|---|---|
| Test Material | Number of Reactors | 0 | 1 | 2 | 3 | 4 | 5 | 6 | 7 | 8 |
| E | 13 | 1787 | 13 | 0 | 0 | 0 | 0 | 0 | 0 | 0 |
| F | 26 | 1774 | 23 | 2 | 1 | 0 | 0 | 0 | 0 | 0 |
| G | 25 | 1775 | 22 | 1 | 2 | 0 | 0 | 0 | 0 | 0 |
| H | 25 | 1775 | 21 | 2 | 2 | 0 | 0 | 0 | 0 | 0 |
| K | 20 | 1777 | 19 | 4 | 0 | 0 | 0 | 0 | 0 | 0 |
| L | 24 | 1776 | 22 | 2 | 0 | 0 | 0 | 0 | 0 | 0 |

From the data in Table VI it is clear that 5-bromo-5-nitro-1,3-dioxane showed a marked sensitizing effect wherein 11 of the 200 subjects were evaluated as being sensitive to a 0.1 percent concentration of the compound on the challenge test, while none of the 200 subjects challenged with a 0.1 percent concentration of 5-bromo-2-methyl-5-nitro-1,3-dioxane were considered to be sensitive to the latter compound. A reading of 5 or more on the 8-point scale was deemed to be indicative of the development of skin sensitization to the test compound. Moreover, the irritation readings associated with the prior art compound were more severe than those recorded for the 2-methyl derivative thereof.

The novel compounds of this invention have the important property of being soluble in water to the extent of about 1.5 percent and in mineral oil to the extent of about 1.1 percent. This valuable property makes such compounds highly useful as antimicrobial agents for preserving cosmetic cream formulations. Effective preservation of a cosmetic cream can be accomplished by incorporating from about 0.01 to about 1.5, preferably from about 0.1 to about 1.0 percent of such compounds therewith. The preparation of a typical cosmetic base cream utilizing 5-bromo-2-methyl-5-nitro-1,3-dioxane at 0.1 percent as a preservative is exemplified in Example 5.

EXAMPLE 5

Seven and one-half kilograms of a non-ionic surfactant cosmetic base cream are prepared as follows:
Add to a first suitable container, Phase I
Mineral oil, heavy — 1,875 g.
Cetyl alcohol — 300 g.

White wax — 450 g.
Lanolin, anhydrous — 225 g.
Sorbitan monosterate — 300 g.
Polyoxyethylene (20) sorbitan monosterate — 450 g.
Heat Phase I to 80° C. with continuous stirring.
Add to a second suitable container, Phase II
Purified water — 3,750 ml.
Heat Phase II to 80° C.
Add Phase I to Phase II with continuous stirring,
Remove heat and allow lot to cool to 45° C. with continuous stirring.
Add to a third suitable container, Phase III
Polyethylene glycol 200 — 93.7 g.
5-bromo-2-methyl-5-nitro-1,3-dioxane — 7.5 g.
Heat to 45° C. to dissolve with stirring.
Add Phase III to the lot at 45° C.
Mix well with continuous stirring.
Q. S. lot to 7.5 kg. with:
Purified water — 200 ml.
Cool to 37° C. with continuous stirring.

In another embodiment of this invention the compound 5-bromo-2,2-dimethyl-5-nitro-1,3-dioxane is an effective antimicrobial, useful for incorporation into such compositions as cosmetics and pharmaceuticals as a preservative. In addition, this useful compound is effective as an antimicrobial in such diverse compositions as adhesives, paints, both oil and water based, particularly latex, detergents, soaps, toilet, laundry, industrial, and others, shampoos, cutting oils, antiseptic and sanitizing chemicals, and the like.

The compound 5-bromo-2,2-dimethyl-5-nitro-1,3-dioxane can be prepared from contacting the 2-bromo-2-nitropropane-1,3-diol of Preparation 1 described above with acetone. Example 6, details this preparation.

EXAMPLE 6

To a 100 ml. 3-necked flask equipped with magnetic stirring was added 20 g. (0.1 mole) of 2-bromo-2-nitropropane-1,3-diol and 30 ml. (0.5 mole) of acetone. After solution was complete, the temperature was 15° C. Then 13 ml. (0.1 mole) of boron trifluoride etherate was added to the reaction mixture from a dropping funnel over a period of about 2 minutes. The temperature rose to 47° C. and then dropped to 35° C. over a period of 10 minutes. The reaction mixture was then poured into 150 ml. of a saturated sodium bicarbonate solution and stirred for 15 minutes. The solids were filtered and washed with 200 ml. acetone, dried and an IR showed a reaction had occurred. About 18 g. of crude material was dissolved in 150 ml. of hot hexane and filtered. On cooling and standing overnight 9.0 g. (40% yield) of 5-bromo-2,2-dimethyl-5-nitro-1,3-dioxane was obtained as pure white needles. An NMR and IR confirmed the structure. An elemental analysis disclosed the following percentage composition:

C: calc. 30.02, found 29.94;
H: calc. 4.20, found 4.26;
N: calc. 5.83, found 6.05;
Br: calc. 33.29, found 33.50.

The antimicrobial activities of 5-nitro-2,2-dimethyl-5-nitro-1,3-dioxane (Compound G) were determined concurrently with 5-bromo-2-methyl-5-nitro-1,3-dioxane (Compound C) and 5-bromo-5-nitro-1,3-dioxane (Compound B) against the same six organisms shown in Table II. Compounds B, C and G showed similar effectiveness. The tests were in vitro determinations utilizing agar plates containing the active compound at 10, 25 and 50 mcg. per ml. of agar. The organisms, at concentrations of $10^6$ organisms per millimeter, were streaked on the solidified agar. The plates were incubated for 24 hours and the presence or absence of growth noted. The minimum inhibitory concentration (MIC) was determined as the lowest active compound concentration in the agar where no growth occurred. Table VII shows the results of this test.

TABLE VII

In Vitro Antimicrobial Activity
Minimum Inhibitory Concentration, mcg./ml. when tested with —

| | Pseudomonas aeruginosa | Streptococcus faecalis | Staphylococcus aureus | Escherichia coli | Candida albicans | Aspergillus niger |
|---|---|---|---|---|---|---|
| Compound B | 25 | <10 | 25 | <10 | 25 | 50 |
| Compound C | 25 | 12.5 | 12.5 | 12.5 | 6.25 | 12.5 |
| Compound G | 50 | 25 | 25 | 25 | 25 | 50 |

Useful compounds of the formula

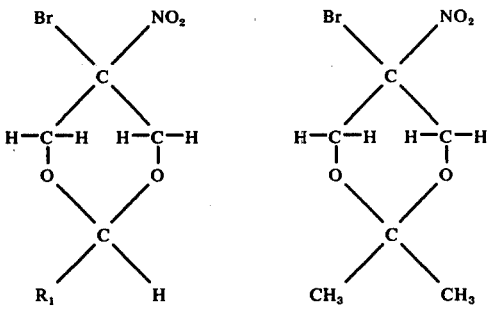

wherein
$R_1$ is methyl, ethyl, n-propyl, or isopropyl are effective antimicrobials for the prevention of the growth of microorganisms selected from the group of gram-positive, gram-negative bacteria and fungi. The growth of such microorganisms can be prevented by contacting said microorganisms with an amount of such compounds effective to prevent such growth. Effective amounts of such compounds will range from as little as about 0.01 percent to about 2.0 percent by weight of the composition to which such compounds are added, preferably from about 0.1 percent to about 1.0 percent.

Typical of such compositions and the concentration of such useful compounds incorporated therein are the diverse products outlined in Examples 7-13.

Examples 7-13

| Antimicrobial Solution: | |
|---|---|
| 95% SD3A Alcohol | 50 parts |
| Water, deionized | 49.5 parts |
| 5-Bromo-2,2-dimethyl-5-nitro-1,3-dioxane | 0.5 part |
| Antimicrobial Ointments: | |
| Polyethylene glycol 300 | 49.5 parts |
| Polyethylene glycol 1500 | 49.5 parts |
| 5-Bromo-5-nitro-2-n-propyl-1,3-dioxane | 1.0 part |
| Antimicrobial Powder: | |
| Talcum, U.S.P. | 99 parts |
| 5-Bromo-2-methyl-5-nitro- | |

Examples 7-13-continued

|  |  |
|---|---|
| 1,3-dioxane | 1 part |
| Shampoo: | |
| Sodium laurylsulfate | 40 parts |
| Coconut fatty acid diethanolamide | 6 parts |
| Water, deionized | 53 parts |
| 5-Bromo-2-ethyl-5-nitro-1,3-dioxane | 1 part |
| Antimicrobial Soap: | |
| Coconut oil glycerides, sodium salt | 60 parts |
| Tallow glycerides, sodium salt | 39 parts |
| 5-Bromo-2-methyl-5-nitro-1,3-dioxane | 1 part |

Other antimicrobial applications and uses of the useful compounds of this invention will be readily recognized by those skilled in the art. The preceding specific examples are illustrative of the practice of this invention and are to be understood as imposing no limitation on the spirit of the invention or the scope of the claims thereto.

What is claimed is:

1. A compound of the formula

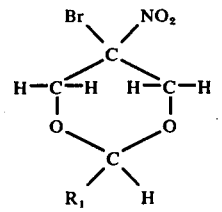

wherein
  $R_1$ is methyl, ethyl, n-propyl, or isopropyl;
2. A compound according to claim 1 wherein the compound is 5-bromo-2-methyl-5-nitro-1,3-dioxane.
3. A compound according to claim 1 wherein the compound is 5-bromo-2-ethyl-5-nitro-1,3-dioxane.
4. A compound according to claim 1 wherein the compound is 5-bromo-5-nitro-2-n-propyl-1,3-dioxane.
5. A compound according to claim 1 wherein the compound is 5-bromo-2-isopropyl-5-nitro-1,3-dioxane.

* * * * *

UNITED STATES PATENT AND TRADEMARK OFFICE
CERTIFICATE OF CORRECTION

PATENT NO. : 4,025,533                    Page 1 of 3

DATED      : May 24, 1977

INVENTOR(S) : Lewis C. Lappas, et al.

It is certified that error appears in the above-identified patent and that said Letters Patent are hereby corrected as shown below:

Column 3, line 48, delete "0245" after "... 5-nitro-".

Column 3, line 66, "outline" should read --outlined--.

Column 4, line 15, "outline" should read -- outlined--.

Column 5, line 18, Table I, the third column heading, "Esterichia coli" should read -- Escherichia coli--.

Column 8, line 34, Table VI, the last summary of test scores was omitted. Insert

--

| Test Material | Number Reactors | Challenge Application Total Number of Reactions with Scores of: | | | | | | | | |
|---|---|---|---|---|---|---|---|---|---|---|
| | | 0 | 1 | 2 | 3 | 4 | 5 | 6 | 7 | 8 |
| E | 0 | 200 | 0 | 0 | 0 | 0 | 0 | 0 | 0 | 0 |
| F | 0 | 200 | 0 | 0 | 0 | 0 | 0 | 0 | 0 | 0 |
| G | 0 | 200 | 0 | 0 | 0 | 0 | 0 | 0 | 0 | 0 |
| H | 2 | 198 | 2 | 0 | 0 | 0 | 0 | 0 | 0 | 0 |
| K | 1 | 199 | 1 | 0 | 0 | 0 | 0 | 0 | 0 | 0 |
| L | 2 | 198 | 2 | 0 | 0 | 0 | 0 | 0 | 0 | 0 |

--, before line 35, "From the data ...".

UNITED STATES PATENT AND TRADEMARK OFFICE
CERTIFICATE OF CORRECTION

PATENT NO. : 4,025,533

DATED : May 24, 1977

INVENTOR(S) : Lewis C. Lappas, et al.

It is certified that error appears in the above-identified patent and that said Letters Patent are hereby corrected as shown below:

Column 11, line 13, under the heading, Examples 7-13-continued, the remaining diverse products were omitted. Insert

--

Antimicrobial Cleaning Composition:

| | |
|---|---|
| Fatty alcohol sulfate (sodium sulfate) | 25 parts |
| Sodium carbonate | 7 parts |
| Sodium sulfate | 15 parts |
| Trisodium phosphate | 40 parts |
| Pentasodium aminotrimethylenephosphate | 10 parts |
| Carboxymethylcellulose | 1 part |
| 5-Bromo-2,2-dimethyl-5-nitro-1,3-dioxane | 2 parts |

UNITED STATES PATENT AND TRADEMARK OFFICE
CERTIFICATE OF CORRECTION

PATENT NO. : 4,025,533  
DATED : May 24, 1977  
INVENTOR(S) : Lewis C. Lappas, et al.

Page 3 of 3

It is certified that error appears in the above-identified patent and that said Letters Patent are hereby corrected as shown below:

Antifungal Latex Paint:

| | |
|---|---|
| Polyvinyl acetate, emulsified | 20 parts |
| Water, deionized | 78 parts |
| 5-Bromo-2-ethyl-5-nitro-1,3-dioxane | 2 parts --, | before line 15, "Other antimicrobial applications ...".

Signed and Sealed this

Twenty-fourth Day of July 1979

[SEAL]

Attest:

Attesting Officer

LUTRELLE F. PARKER  
Acting Commissioner of Patents and Trademarks